(12) United States Patent
Noble et al.

(10) Patent No.: US 12,127,936 B2
(45) Date of Patent: Oct. 29, 2024

(54) IMPLANT WITH ARTICULATING SECTIONS

(71) Applicant: PORIFEROUS, LLC, Newnan, GA (US)

(72) Inventors: Aaron M. Noble, Newnan, GA (US); Roee Landsberg, Tel-Aviv (IL)

(73) Assignee: Poriferous, LLC, Newnan, GA (US)

(*) Notice: Subject to any disclaimer, the term of this patent is extended or adjusted under 35 U.S.C. 154(b) by 0 days.

(21) Appl. No.: 17/689,572

(22) Filed: Mar. 8, 2022

(65) Prior Publication Data
US 2022/0280286 A1 Sep. 8, 2022

Related U.S. Application Data

(60) Provisional application No. 63/158,177, filed on Mar. 8, 2021.

(51) Int. Cl.
*A61F 2/18* (2006.01)
*A61F 2/44* (2006.01)

(52) U.S. Cl.
CPC ............. *A61F 2/186* (2013.01); *A61F 2/441* (2013.01); *A61F 2230/0006* (2013.01); *A61F 2230/0076* (2013.01); *A61F 2250/0003* (2013.01); *A61F 2250/0006* (2013.01); *A61F 2250/0023* (2013.01); *A61F 2250/0024* (2013.01); *A61F 2250/0039* (2013.01); *A61F 2250/0067* (2013.01); *A61F 2250/0068* (2013.01)

(58) Field of Classification Search
CPC ............. A61F 2/186; A61F 2250/0003; A61F 2250/0023–0024; A61F 2/441; A61F 2230/0076; A61F 2250/0039
See application file for complete search history.

(56) References Cited

U.S. PATENT DOCUMENTS

| 2005/0245906 A1* | 11/2005 | Makower | A61M 31/002 |
| | | | 604/892.1 |
| 2005/0273060 A1* | 12/2005 | Levy | A61F 5/0083 |
| | | | 623/23.67 |
| 2012/0191125 A1* | 7/2012 | Babkes | A61F 5/0036 |
| | | | 606/192 |

(Continued)

OTHER PUBLICATIONS

International Patent Application No. PCT/US2022/019328, International Search Report and Written Opinion dated Aug. 22, 2022, 17 pages.

(Continued)

*Primary Examiner* — Rebecca S Preston
(74) *Attorney, Agent, or Firm* — Kilpatrick Townsend & Stockton LLP

(57) ABSTRACT

An implant that has a central body or core that functions as a spine, with extending articulating segments that extend from the spine. The articulating segments define a space between each section to allow the implant to be compressed and bent, such that the space between each section can be compressed or expanded. A specific use for the implant is as a sinus implant. Specific embodiments of the implant are useful in correcting missing tissue in the inferior turbinate. Specific embodiments are sized and shaped to treat empty nose syndrome (ENS). Embodiments also relate to an implant that has a port for allowing various fluids or solutions to be flushed into the implant and released through the implant surface.

5 Claims, 4 Drawing Sheets

(56) References Cited

U.S. PATENT DOCUMENTS

| | | | |
|---|---|---|---|
| 2014/0277043 A1* | 9/2014 | Jenkins | A61B 34/30 |
| | | | 134/6 |
| 2017/0056602 A1 | 3/2017 | Medina et al. | |
| 2017/0325949 A1* | 11/2017 | Rodgers | A61F 2/2421 |

OTHER PUBLICATIONS

International Patent Application No. PCT/US2022/019328, Invitation to Pay Additional Fees and Partial International Search Report dated Jun. 7, 2022, 4 pages.

* cited by examiner

SECTION B-B
SCALE 1 : 1

DETAIL B
SCALE 10 : 1

IMPLANT WITH ARTICULATING SECTIONS

CROSS REFERENCE TO RELATED APPLICATIONS

This application claims the benefit to U.S. Provisional Application No. 63/158,177, filed Mar. 8, 2021 entitled "IMPLANT," the entire disclosure of which is hereby incorporated by reference in its entirety.

FIELD OF THE DISCLOSURE

Embodiments of the present disclosure relate generally to an implant that has a central body or core that functions as a spine, with extending articulating segments that extend from the spine. The articulating segments define a space between each section to allow the implant to be compressed and bent, such that the space between each section can be compressed or expanded. A specific use for the implant is as a sinus implant. Specific embodiments of the implant are useful in correcting missing tissue in the inferior turbinate. Specific embodiments are sized and shaped to treat empty nose syndrome (ENS). Embodiments also relate to an implant that has a port for allowing various fluids or solutions to be flushed into the implant and released through the implant surface.

BACKGROUND

Empty nose syndrome (ENS) is a rare syndrome of chronic nasal physiologic impairment that can be caused by an overly aggressive turbinate reductive procedure. It relates to nasal tissue loss. Although not every patient undergoing a radical turbinate procedure experiences ENS symptoms, when it occurs, ENS affects the normal breathing function of the nasal cavity. Patients with ENS experience mucosal dryness, nasal congestion, facial pain and headaches, excessive crusting and discharge, although symptoms can vary among patients. Individuals may also experience differences in the amount of airflow and resistance between bilateral nasal cavities.

It has traditionally been difficult to treat or control the symptoms of ENS. Conservative treatments include nasal irrigation, nasal moisturizing treatments, and plugging of the nasal cavity. Surgical treatment, in which synthetic implant materials or implantation of cartilage are submucosally implanted have been attempted. Additionally, other types of surgical treatments have aimed to decrease the size of the nasal cavities, promote regeneration of normal mucosa, increase lubrication of dry mucosa, and improve vascularity of the nasal cavities. Improvements to implants and treatments are desirable.

SUMMARY

Embodiments of the present disclosure provide a flexible implant capable of taking the shape of the inferior turbinate or any other implant shape for a similar or different application. This disclosure also relates to implants that have one or more ports for allowing various fluids or solutions to be flushed into the implant and released through the implant surface.

Certain embodiments provide an implant, comprising a central body and a plurality of segments extending from the central body. Certain embodiments find particular use as a sinus implant. Each segment of the plurality of segments may have a circular outer circumference. In a specific example, the central body and the plurality of segments comprise porous polyethylene. It is possible for the central body to have a port, which can be used for delivering flushing fluids, medications, glue, or any other appropriate material into the implant such that the fluids/material flow out of external pores of the implant (either flowing out of the central body, the plurality of segments, or both). In a specific example, the implant can have a first porosity at a central portion/core of the implant body and a second porosity at portions of the implant closer to its external surface, wherein the first porosity is larger than the second porosity.

DESCRIPTION

Figure 1A:
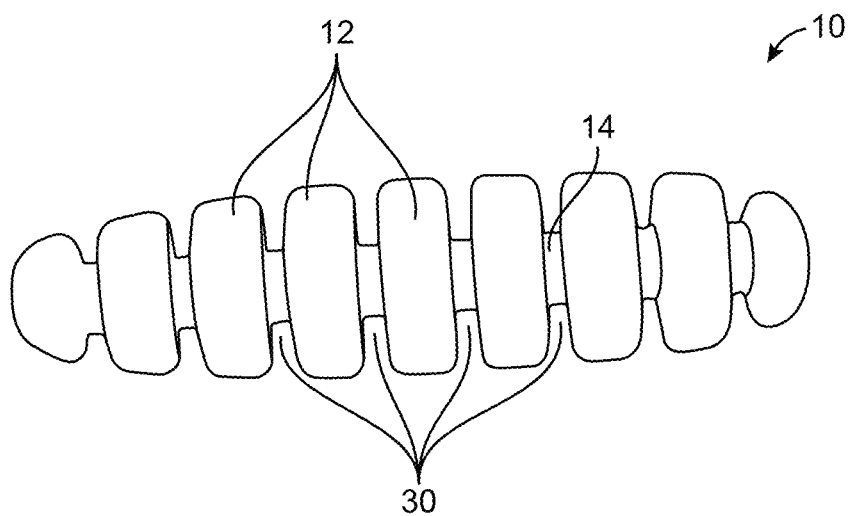
FIG. 1A shows a side perspective view of one embodiment of an implant disclosed herein.

Implant with articulating segments.

Embodiments of the present disclosure provide a flexible implant 10 capable of taking the shape of the inferior turbinate or any other implant shape for a similar or different application. The disclosed implant 10 comprises of a series of a plurality of three-dimensional segments 12 connected by a central body 14 (which may also be referred to as a "central core" or "central spine" or "central body core"). Space between the three-dimensional shapes can allow for compression and expansion of these segments 12, which allows them to function as joints, respectively, allowing the implant shape to be contoured in three-dimensional space, such as the shape of the inferior turbinate. The implant 10 can be bent or curved so that the central body 14 moves, causing the segments 12 to articulate or otherwise move with respect to one another. The three-dimensional segments 12 may generally have a circular outer perimeter 16 which can allow for ease of placement of the implant within the nasal cavity. The three-dimensional shapes 12 may have a tapered appearance along the length of the implant. For example, shapes/joints positioned along ends 18 of the implant may have a smaller diameter than shapes/joints positioned toward the middle portion 20 of the implant. This is illustrated by the figures.

Port.

This disclosure also relates to implants that have one or more ports 22 for allowing various fluids or solutions to be flushed into the implant and released through the implant surface. Although the port concept is described with respect to the disclosed implant herein, it should be understood that the present disclosure of a port 22 for flushing may be used with other types of implants. For example, in addition to a sinus or turbinate implant, one or more ports 22 as disclosed herein may be used with a chin implant, an ocular implant, a mandible implant, or any other type of craniofacial implant. In addition to these types of implants, the disclosed port may be used with implants for other parts of the body. Non-limiting examples include a knee, ankle, shoulder, elbow, hip, finger, toe, spine, or any other types of implant that may benefit from injection of a fluid into the implant. The disclosed port 22 may be useful in connection with porous materials, such as the porous polyethylene material described herein. The pore sizes can be modified as described below in order to encourage flushing of fluid through the implant and/or to help equalize pressure of the fluid as it exits pores of the implant.

In one specific example, the implant may be provided with a pre-molded hole or port 22 that allows a rod or hypodermic needle or any other insertion member 50 to be inserted into the hole or port with a slight interference fit. This fit can allow for easier handling of the shape intraoperatively. It can also serve as a port where a fluid, such as saline with antibiotic, or any other appropriate fluid, can be injected into the central portion 24 of the implant. This can serve to flush the implant clean of any contamination picked up during insertion into the nasal cavity and into the implant pocket, respectively.

The hole or port may also be used for drug delivery. The hole or port may be used for flushing the implant. The hole or port may be used to deliver a surgical glue that may help set the implant in place with respect to the defect being repaired. The hole or port may be used for stabilization of the implant and ease of use.

During surgery, it is can generally be difficult for surgeons to manipulate and hold small implants and make accurate intraoperative modifications with surgical scalpels, scissors, or burrs. The ability to insert a hypodermic needle into the implant can allow the needle (and its corresponding components, such as a syringe and plunger) to serve as a handle that can protect the surgeon's fingers from cutting. This can also provide better control during the shaping process.

Additionally, a syringe can be filled with sterile saline, saline with mixture of antibiotic such as erythromycin, or any other appropriate surgical fluid that could be useful for injection. For example, other fluid substances could prove to be beneficial, such as various types of surgical glues or other solutions.

In the example of surgical glue, this may serve as a less invasive method of fixation of the implant until the point where the body can grow fibrovascular tissue and help to eliminate implant migration. Benefits of such surgical glue injected within the porous body of the implant may also include the addition of the glue products anti-infection substance.

The injected material can also be of medicinal purpose. One example of this would be for ongoing treatment for cancer when an implant is used for replacement of a malignant or cancerous craniomaxillofacial segment to serve as a drug delivery vessel. Clinical literature discusses that small open spaces of subcutaneous tissue at the tissue implant interface improve the uptake of fluid, even at relativity low flow rates or pressure. This has shown to be significant in devices used to treat glaucoma. Studies conclude that the fibrovascular network in communication with this micro separated space provides fluid flow, even after full tissue integration occurred.

Accordingly, one example of this port is for use with a porous polyethylene implant may be used to introduce an implant/medicinal fluid to the subcutaneous space, while having a sealed port for a cannula or shunt. In diabetics, short term subcutaneous insertion of a polymeric cannula for insulin delivery must be removed and replaced every four to five days due to the fibrous capsule that grows around the foreign alloplastic material.

In another surgical model, it has been shown that improvement of fluid dispersion in the glaucoma valve model, having a porous outer layer that integrates with the surrounding tissue can be beneficial. It is also possible that a cylinder or tapered tip may help improve insertion and reduce trauma to proximal tissue.

In the implant described herein, the port 22 may be formed within the central body 14 and can provide an interference fit between the inner port 22 at an outer end 18 of the implant, having an interference, sealing fit to a needle, shunt, cannula, or any other insertion device 50 (or a holding device or rod) that may be inserted into the port. The interference fit may be restricted in engagement length by the ideal contact area for stabilizing the implant and providing a good seal.

It is possible to use the disclosed implant to deliver treatments. For example, a rod 50 may be inserted into the port for securement. The rod may have a larger area around the remaining length of the rod serving to deliver a drug, such as insulin. For diabetics, this process of insulin delivery is life-long. The skin is repeatedly injured and a scar capsule forms at the insertion point. The proposed device may be provided with a rod that is sufficient to also serve as a handle or lever, and this may serve well to retract the integrated delivery device.

Although removal of a tissue-integrated device may seem to be overly disruptive to the implant tissue interface, this process actually leaves the insertion site free of the remnant fibrovascular capsule as currently occurs with needles, canulla, or shunts, that have been inserted in the subcutaneous space for over three days.

As illustrated by the below figures, the disclosed turbinate implant can have spaces 30 between each segment 12 to allow the implant 10 to be contoured to the patient's anatomy. Bending the implant one way compresses the space 30, bending the implant 10 another way can create an expanded space, as shown by FIG. 1B. In one example, the implant is intended for implantation as a sinus implant, and thus is a non-loadbearing implant. In a specific embodiment, the implant includes nine one mm slices or segments 12 that travel down a 3 mm central body core 14 that runs the length of the implant. It has been found that this design can allow the implant to contour easily.

Figure 1B:
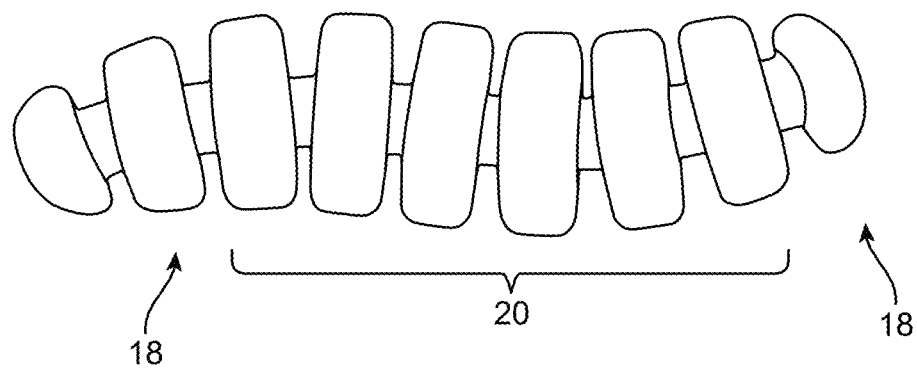
FIG. 1B shows a side perspective view of the implant of FIG. 1A in a bent configuration.
Figure 2:
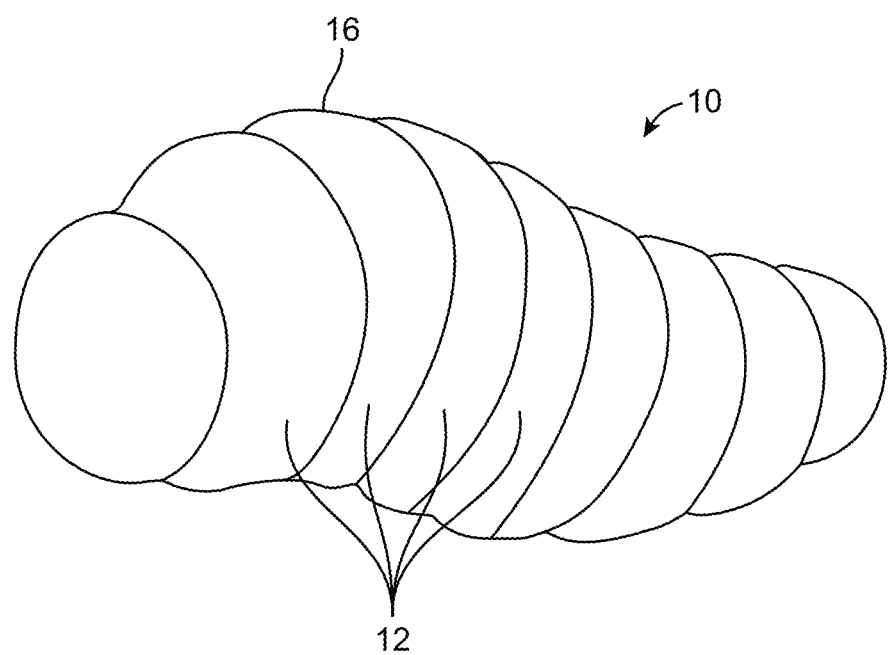
FIG. 2 shows a front perspective view of the implant of FIG. 1A.
Figure 3A:
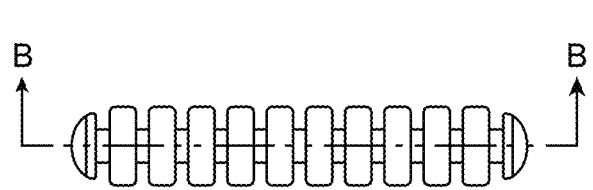
FIG. 3A shows a side plan view of one embodiment of an implant disclosed herein.
Figure 3C:
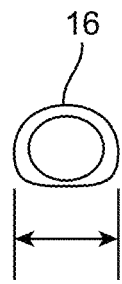
FIG. 3C shows a front plan view of the implant of FIG. 3A.
Figure 3B:
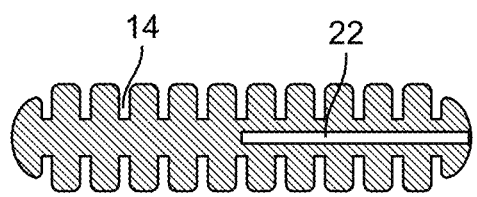
FIG. 3B shows a side cross-sectional view of the implant of FIG. 3A, illustrating the presence of a port.
Figure 5:
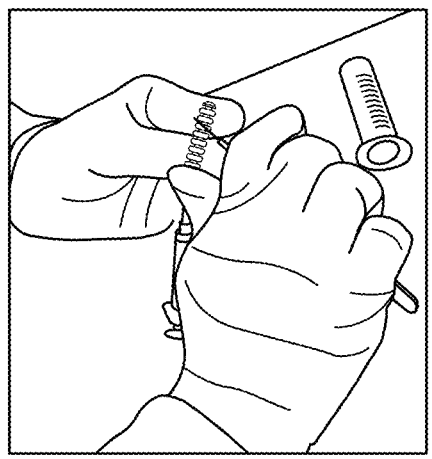
FIG. 5 shows the option of a surgeon shaping an implant.

FIGS. 1A and 1B illustrate side views of the implant 10. These figures shows the central body 14 core or "spine" running the length of the implant. Extending from the central core is a plurality of segments 12 or elements. These segments 12 generally have a circular outer circumference 16, as can be seen in FIGS. 2-3. In some examples, segments 12 provided at ends 18 of the implant 10 have a smaller diameter than elements toward the middle portion 20 of the implant. This tapering at the ends can help insertion. In other examples, the segments 12 all have a similar diameter. In other examples, the segments 12 need not be circular, but may be oval-shaped, elliptically-shaped, rounded-edge triangular shaped, or may have any other appropriate shape. In some examples, a surgeon may use a scalpel to shave or otherwise initiate edges of the elements as desired. One example of the shaping option is illustrated by FIG. 5.

The central body 14 may be non-porous or may have a non-porous inner body (ROD). Exemplary materials may be polyethylene. This can increase strength and prevent the device from breaking when/if over bent. Alternatively, the central core may be porous. Exemplary pore sizes and gradients are described below.

The following examples provide exemplary dimensions, but it should be understood that these examples are provided for exemplary purposes only and are not intended to be limiting in any way. In one example, the central core or "spine" has a diameter of about 3 mm. Each element may have a diameter of about 5-12 mm. In a specific example, the diameter of each element is about 6.5-9 mm. The space between each element may be about 1 mm. (This is generally measured when the element is in its unbent configuration of FIG. 1A. The space will lessen or enlarge when the implant is bent, as shown by FIG. 1B.) The length of the entire implant may be about 25-50 mm. In a specific example, the length of the implant is about 35 mm. In one specific example, the diameter of the central body core itself (without considering the outer perimeter of the segments) may be about 5-8 millimeters. In a specific example, the diameter of the central core itself is about 6.5 mm. In one specific example, the total diameter of the implant itself (including the outer perimeter of the segments, with the total diameter measured as the outer perimeter of the segments) may be about 6-10 millimeters. In one specific example, the diameter of the implant is about 8-9 millimeters.

Figure 4:
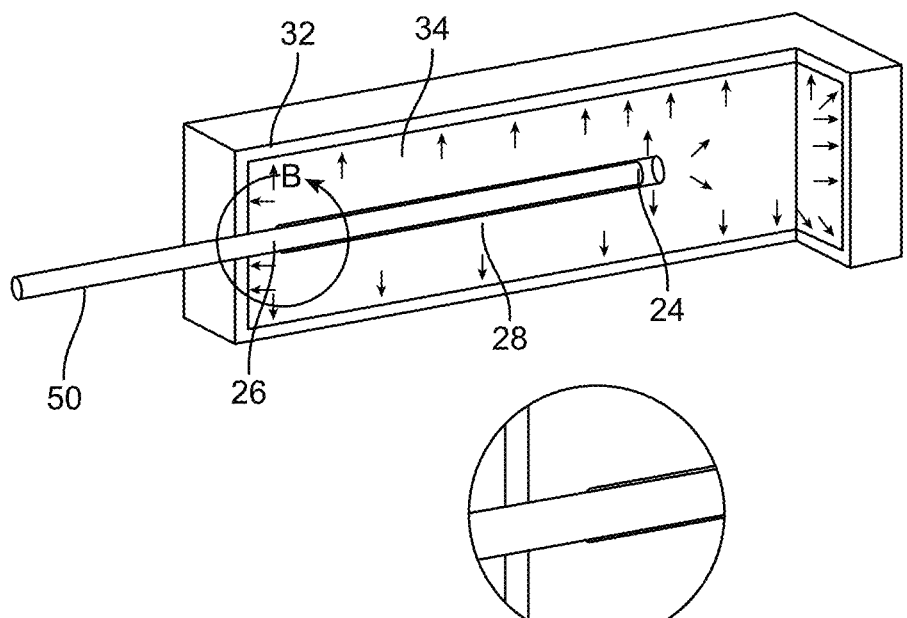
FIG. 4 shows a cross-sectional schematic view of a needle, a fluid or medication delivery component, or a holding component inserted into the port of FIG. 3B.

Referring now to FIGS. 3 and 4, a pre-molded hole or port 22 may be provided along at least a portion of the central core 14 in order to receive a needle for holding the implant during shaping, for flushing contaminants from the implant, or for insertion and removal of the implant. The port 22 may extend about half-way through the spine. (It is also possible for the port to extend further into the implant or a shorter distance into the implant.) If the port is used for a differently shaped implant, it may be desirable for the port to be positioned at a central location to help ease its use and to help ensure an even distribution/exit of fluid from all surfaces of the implant at a generally equalized pressure. Although the port 22 is shown as having an entrance at one end of the implant, it is possible for the port to have one or more entrances positioned between one or more of the plurality of segments.

Figure 6:
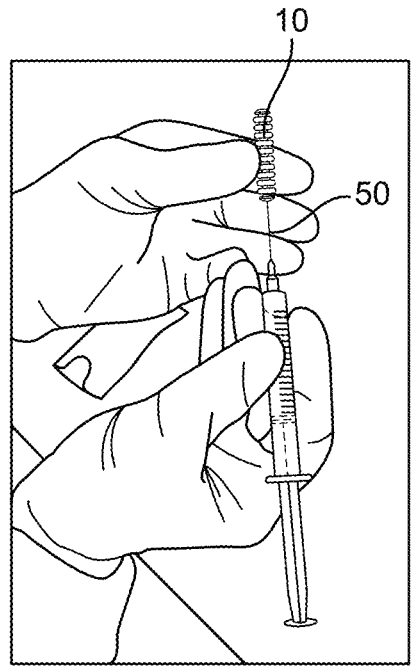
FIG. 6 shows insertion of a needle into a port of an implant.
Figure 7:
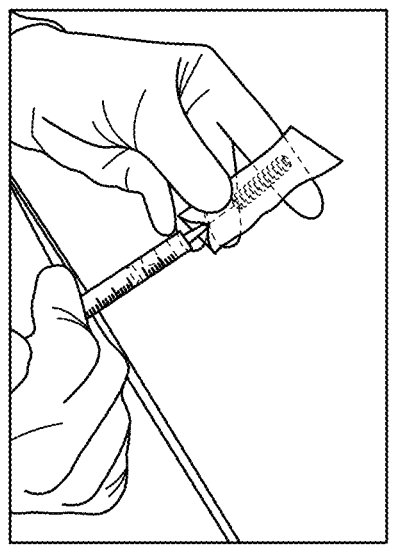
FIG. 7 shows delivery of fluid into the port of the implant of FIG. 6.

The external segments 12 of the implant may be shaped (e.g., cut or shaved to change their external circumference) prior to insertion of a needle into the port, or the needle may be used to help support the implant during shaping. FIG. 5 shows optional shaping of the implant prior to insertion. FIG. 6 illustrates insertion of a needle 50 into the pre-molded hole or port. FIG. 7 illustrates injection of fluid through the port. The fluid is delivered through a syringe or IV fluid bag into the implant. The entrance 26 to the port 22 should be sized such that it creates a tight interference fit with the needle 50 in order to stabilize the needle and form a good seal around the needle shaft. As shown by FIG. 4, the internal channel 28 of the port 22 generally has an inner clearance that is just slightly larger than the entrance 26, which makes it easier to inject fluid into the channel 28 of the port 22.

It is possible for porosity of the implant to be consistent throughout. In another example, however, it is possible for porosity of the implant to be altered in order to help obtain a constant flow of fluid through and out of the implant. As illustrated by FIG. 4, there may be an outer layer 32 of smaller pores along the outer external surface (or closer to the external surface than the core interior 34 of the implant body) of the central body 14. The core interior 34 may have a first porosity of larger pore sizes that allow fluid to flow with less restriction through the implant. The second porosity of the pores at the outer layer/external surface 32 are generally smaller than the first porosity. The porosity may also be a gradient, such that the porosities change as they reach the external surface 32 (i.e., rather than providing only two different pore sizes, it is possible for the pore sizes to gradually decrease as they extend toward the external surface of the implant body.) In use, this allows fluid to flow evenly and relatively quickly to the outer layer of pores, but the outer layer of smaller pores requires a higher pressure for the fluid to exit, creating a more constant flow and equalized pressure. This allows the flow of fluid out of the implant to function much like an air stone that is positioned under water. Providing an outer layer 32 of smaller porosity allows the fluid pressure to equalize within the large pore area (in the core interior 34), and then the capillary restriction of the smaller pore outer layer forces the fluid to flow equally around the body of the implant device.

Outer layer 32 pore sizes may range from about 40 µm to about 120 µm. It is understood that a pore size of about 100 µm is ideal for fibrovascular tissue integration. In one example, the pore sizes may range from 40 µm to 120 µm, with the outer layer being sufficiently small enough to resist the injected fluid, as described above. Fluid can be internally mixed with a thickening agent to improve this effect while carrying antibiotic, flushing fluid, or surgical glue. The inner area 34 may have a larger pore size and less restriction to fluid flow than the outer layer 32.

In a specific embodiment, the pore size of the core interior 34 may range from about 60 µm to 75 µm, depending on the thickest cross section of the implant. Larger pore sizes provide faster fibrovascular integration. The time the body is actively integrating into a device is proportional to the time of healing response.

Providing varying porosities can allow the fluid pressure to equalize within the large pore area, and then the capillary restriction of the smaller pore outer layer forces the fluid to flow equally around the body of the implant device. This is shown schematically by FIG. 4, illustrating that any shape or type of implant is possible for use in connection with this disclosure.

The material of the implant may be porous polyethylene, which allows the patients tissue to grow into the implant for stabilization. The porosity of the implant can be vascular and allow for regulation of temperature and humidity within the nasal cavity. This material has also been found to be malleable which can allow the surgeon flexibility during the surgical implantation process. Other materials are possible and considered within the scope of this disclosure, non-limiting examples of which include porous polytetrafluoroethylene (PTFE), ultra high molecular weight polyethylene (UHMWP), polyether ether ketone (PEEK), or any combination thereof.

Changes and modifications, additions and deletions may be made to the structures and methods recited above and shown in the drawings without departing from the scope or spirit of the disclosure and the following claims.

What is claimed is:

1. An implant, comprising:
   an elongated central body; and
   a plurality of discrete, spaced apart segments extending from the central body;
   the implant comprising a first end, a second end, and a middle portion, the implant tapering from the middle portion to the first and second ends such that one of the segments at the middle portion is larger than one of the segments at the first end and one of the segments at the second end;

wherein the central body defines joints between the segments allowing the implant to be contoured; and wherein the central body and the plurality of segments comprise porous polyethylene.

2. The implant of claim 1, wherein each of the plurality of segments has a circular outer circumference.

3. The implant of claim 1, wherein the implant is configured as a sinus implant.

4. The implant of claim 1, further comprising a port.

5. An implant, comprising:

an elongated central body; and a plurality of discrete, spaced apart segments extending from the central body;

the implant comprising a first end, a second end, and a middle portion, the implant tapering from the middle portion to the first and second ends such that one of the segments at the middle portion is larger than one of the segments at the first end and one of the segments at the second end; wherein the central body defines joints between the segments allowing the implant to be contoured;

wherein the central body defines one or more ports extending from an exterior of the central body into an interior of the central body for receiving fluid; and wherein the central body is porous, wherein the central body comprises pores at the exterior of the central body that are smaller than pores at the interior of the central body.

\* \* \* \* \*